United States Patent
Franken

(10) Patent No.: US 10,321,671 B1
(45) Date of Patent: Jun. 18, 2019

(54) METHOD OF PRODUCING AN INSECT REDUCING COMPOSITION

(71) Applicant: Aunt Fannie Co, Portland, OR (US)

(72) Inventor: Mathew John Franken, Portland, OR (US)

(73) Assignee: Aunt Fannie Co., Portland, OR (US)

(*) Notice: Subject to any disclaimer, the term of this patent is extended or adjusted under 35 U.S.C. 154(b) by 0 days.

(21) Appl. No.: 15/467,732

(22) Filed: Mar. 23, 2017

Related U.S. Application Data

(63) Continuation-in-part of application No. 14/932,934, filed on Nov. 4, 2015, now abandoned, which is a continuation of application No. 14/167,128, filed on Jan. 29, 2014, now abandoned.

(60) Provisional application No. 61/758,619, filed on Jan. 30, 2013.

(51) Int. Cl.
| | | |
|---|---|---|
| *A01N 25/00* | (2006.01) | |
| *A01M 1/20* | (2006.01) | |
| *A01N 37/02* | (2006.01) | |
| *A01N 25/30* | (2006.01) | |
| *A01M 1/02* | (2006.01) | |

(52) U.S. Cl.
CPC ............ *A01M 1/2016* (2013.01); *A01M 1/02* (2013.01); *A01N 25/30* (2013.01); *A01N 37/02* (2013.01)

(58) Field of Classification Search
CPC ...... A01M 2200/011; A01M 2200/012; A01N 25/00; A01N 25/006; A01N 25/30
USPC .......... 43/107, 122, 131, 132.1; 424/405, 84
See application file for complete search history.

(56) References Cited

U.S. PATENT DOCUMENTS

| | | | | |
|---|---|---|---|---|
| 4,217,722 A | * | 8/1980 | McMullen | A01M 1/14 43/114 |
| 2008/0175813 A1 | * | 7/2008 | Kovacs | A01N 65/34 424/84 |
| 2008/0292723 A1 | * | 11/2008 | Crudden | A01N 25/12 424/618 |
| 2012/0321587 A1 | * | 12/2012 | Rosen | A01N 41/02 424/84 |
| 2013/0122120 A1 | * | 5/2013 | Angjeli | A01N 41/02 424/725 |
| 2015/0216182 A1 | * | 8/2015 | Brown | A01N 57/16 424/405 |

* cited by examiner

*Primary Examiner* — Peter M Poon
*Assistant Examiner* — Danielle A Clerkley

(57) ABSTRACT

A composition, device and method of reducing an insect population is disclosed. The composition includes an amphiphilic component, an acetic acid component, and a color component. The device is dimensioned to retain a composition. The device is further dimensioned to define an opening that is smaller than a diameter of the body of the device.

3 Claims, 3 Drawing Sheets

METHOD OF PRODUCING AN INSECT REDUCING COMPOSITION

RELATED APPLICATIONS

The present patent document is a continuation in part of application Ser. No. 14/932,934 filed Nov. 4, 2015 which is a continuation of application Ser. No. 14/167,128, filed Jan. 29, 2014, which claims the benefit of the filing date under 35 U.S.C. § 119(e) of Provisional U.S. Patent Application Ser. No. 61/758,619, filed Jan. 30, 2013. All of the foregoing applications are hereby incorporated by reference

BACKGROUND

Public interest in natural and organic foods has transformed what was once a small market niche into a high growth sector. Consumers increasingly choose fresh foods over packaged and processed foods, and farmer's markets, organic food coops, and similar establishments are flourishing.

Fruit flies are a natural result of keeping fresh fruits and vegetables in the home. Approximately 48 million people per year contract food borne illness. Research has identified fruit flies as a significant vector of *Escherichia Coli* (*E. Coli*) O157:H7, an agent identified in food borne illness. The link between fruit flies and *E. Coli* (and thus food borne illness) create a need for an effective fruit fly extermination device.

BRIEF SUMMARY

We disclose a method, composition, and device for reducing insect infestations. The method, composition, and device includes acetic acid, an amphiphlic compound, and a dye. The device may include a transparency, a body, and an opening. The opening may be smaller than the body of the container.

Other systems, methods, features, and advantages of the disclosure will be, or will become, apparent to one with skill in the art upon examination of the following figures and detailed description. It is intended that all such additional systems, methods, features and advantages be included within this description, be within the scope of the invention, and be protected by the following claims

DETAILED DESCRIPTION

Figure 1:
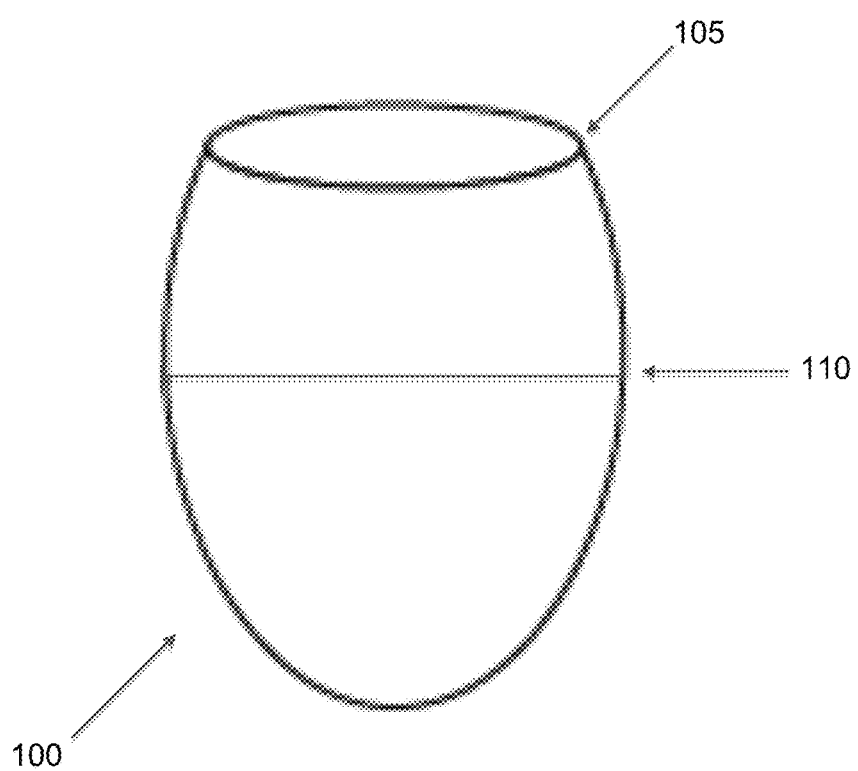
FIG. 1 illustrates an exemplary device.

Approximately 48 million people get sick each year from food borne illness. Due to the overwhelming increase of large scale food recalls, new research has uncovered fruit flies as a significant vector of *Escherichia coli* (*E. coli*) O157:H7, one of the most dangerous food borne health hazards to humans in the developed and undeveloped world. This new found data indicates fruit flies are much more than simply an embarrassing nuisance in the home. They are a threat to our health and safety.

We disclose an all natural method, composition and device for reducing insect populations. For example, the disclosed method, composition, and device may reduce the incidence of bacterial contamination, e.g., of food, by capturing and killing insect carriers of food borne disease agents, such as but not limited to, fruit flies. The presently disclosed method, composition, and device may be more effective as well as more natural, safe, and non-toxic than existing solutions. The disclosed method, composition, and device is the result of years of experimentation.

The FDA is lending much greater concern to the fruit fly population today given the increasing number of large national level recalls. Medical epidemiologists at the National Center for Biotechnology, a government arm of the National Institutes of Health and National Library of Medicine, as well as resource to the FDA and USDA, have found fruit flies contract *E. coli* O157:H7 by ingesting bacteria laden feces and transmit *E. coli* O157:H7 when they lay eggs in or on fruit. Fruit flies puncture the fruit skin with their ovipositors and inject batches of eggs into the fruit wounds. *E. coli* O157:H7 is then subsequently implanted into the fruit and reproduces quickly. The FDA is now focused on the dangerous health hazards associated with fruit flies, both in pre-sale storage, production, and delivery, as well as household contamination. See Mediterranean Fruit Fly as a Potential Vector of Bacterial Pathogens, Appl. Environ. Microbiol. 2005 July; 71(7): 4052-4056 (incorporated by reference herein in its entirety).

The composition for reducing insect population may include acetic acid, water, an amphiphilic agent, (e.g., surfactants) and a coloring agent. The acetic acid component may include but is not limited to vinegar, apple cider vinegar, balsamic vinegar, beer, distilled vinegar, rice vinegar, white vinegar, or wine. In a variation, the composition may include citrus pulp, ethyl lactate, sodium lauryl sulfate, malic acid, and optionally water.

The amphiphilic agent may be dishsoap such as but not limited to that sold under the brand name PALMOLIVE, dish washing soap, hand soap, shampoo, body soap, or otherwise. In a variation, the composition may contain individual components that make up PALMOLIVE, for example but not limited to citrus, sodium lauryl sulfate and lactic acid. In a variation, the lactic acid may be supplied as ethyl lactate, which may separate into lactic acid and ethanol in composition. In a further variation, the citrus may be supplied as citrus pulp. The coloring agent may be food coloring, for example but not limited to, food coloring of a red, pink, or similar color.

In one variation, the composition may include the following: for an approximately 4 ounce amount of composition: 4 ounces of apple cider vinegar, 3-6 drops of red or pink food coloring, and 2-3 drops of amphiphilic agents, for example but not limited to, surfactants, dish soap, hand soap, shampoo, and otherwise. The surfactants may include but is not limited to sodium lauryl sulfate. One of skill in the art would understand that increasing the amount would increase other ingredients proportionally.

The composition of reducing insect population may include a composition of vinegar, coloring, and amphiphilic agent; placing an effective amount of the composition into a container; the container having a body and an opening. The body may have a translucence, for example, the body may be 5-99% translucent. Alternatively or additionally, the body may be opaque colored material, such as glass, plastic, or otherwise. Where the body is opaque, it may have a surface color which may be red, pink, or similar.

FIG. 1 illustrates an exemplary shape of a device for reducing an insect population. The container 100 may have a top portion which may define an opening 105 and a body portion 110. The opening 105 of the container 100 may be smaller than the body 110 of the container. While an oval shape is shown herein, it should be understood that the shape may be changed while preserving an opening smaller than a region of the body.

Figure 2:
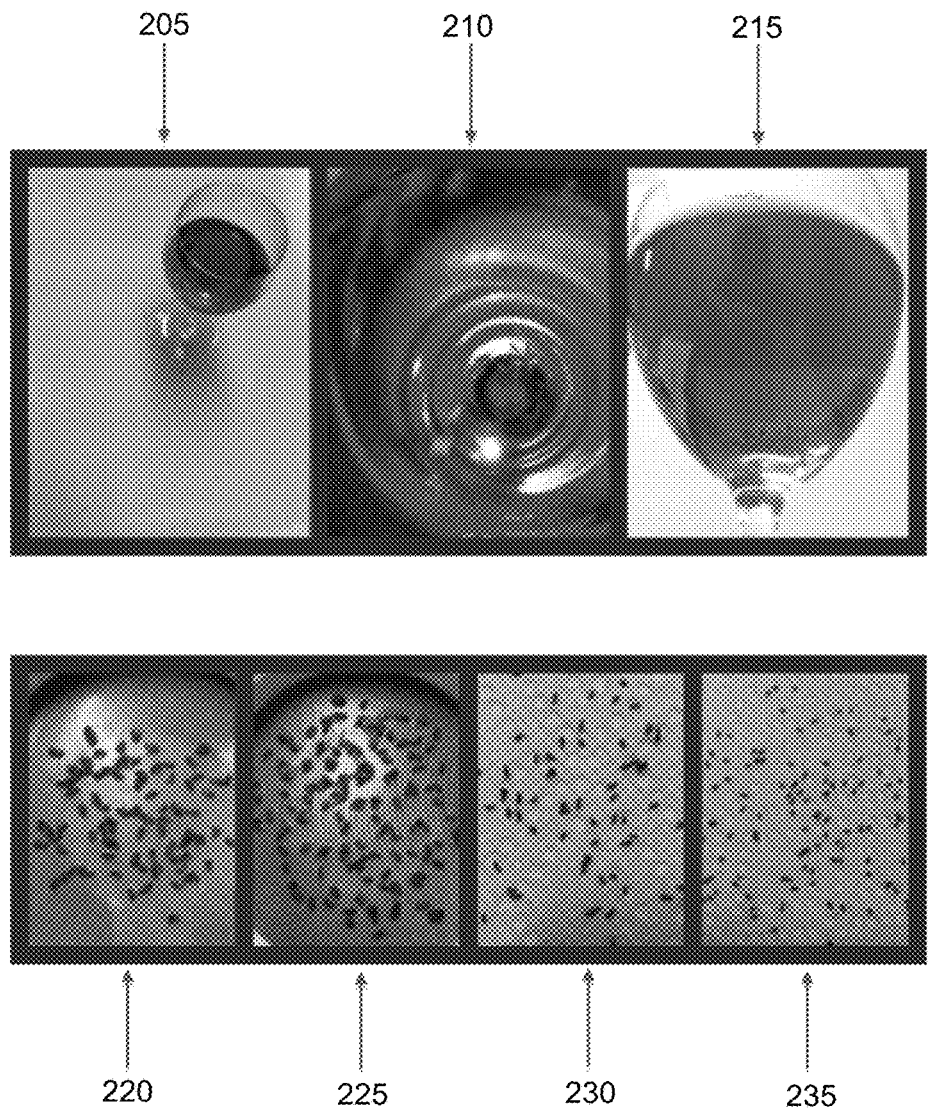
FIG. 2 illustrates experimental data.

FIG. 2 illustrates the effectiveness of the invention. The figure illustrates the amount of flies captured by the composition and device and composition over a 4 hours, 24 hour, and 48 hour time period. The top set of images visually demonstrates the number of flies captured by the composition. From left to right what is shown in 205 is the composition at 0-hour, in 210 the contents of the composition at 4-hour, and at 215 the contents of the composition at 24-hour. The image demonstrates the effectiveness of the composition and device for capturing and containing insects.

FIG. 2 provides a second row of four images. From left to right, at 220 the liquid solution was filtered with a cheesecloth at 24-hour. The flies are visualized on the surface of the filter. In image 225 the solution containing flies is filtered at 48-hour. The flies captured by the device in the 48-hour period are visualized on the surface of the cheese cloth. At image 230, the flies filtered in photo 1, after drying, are more easily visualized and quantified. At image 235, the flies filtered in photo 2, after drying, are more easily visualized.

Figure 3:
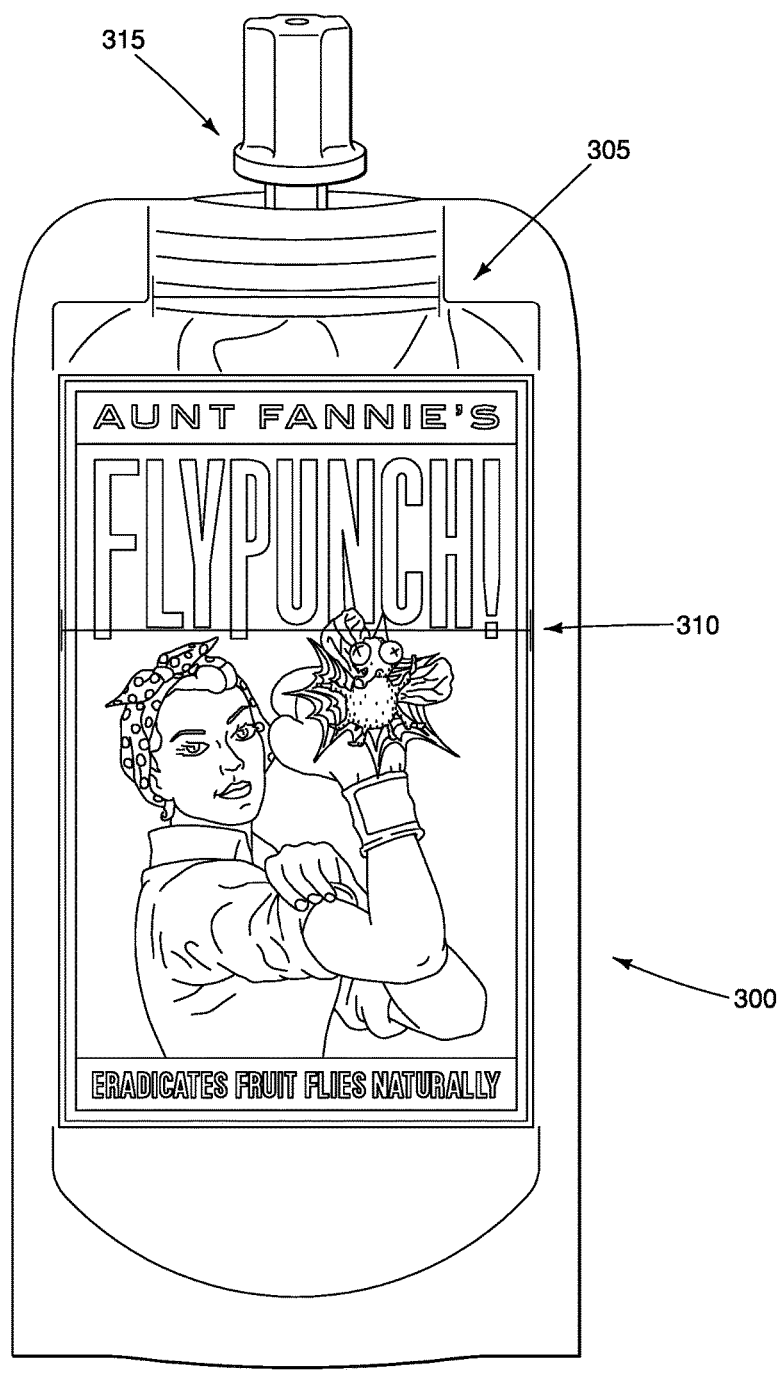
FIG. 3 illustrates an exemplary packaging.

FIG. 3 illustrates an exemplary packaging 300 for the composition. The packing may include a notched-cut on the edge of the package to allow consumers to pour the punch. The stand-up pouch may also be easily stored in a typical pantry, drawer, or cupboard. The packaging may be resealable to store an unused portion for future use. The packing 300 may have a top portion which may define an opening 3155 and a body portion 310. The opening 315 and 305 of the packaging 300 may be smaller than the body 310 of the packaging.

A method of reducing an insect population may include the following steps: obtaining a package of insect reducing composition, opening the packaging, pouring a portion of the contents into a device, the device having an opening that is smaller than a portion of the body, placing the device in an area having insect activity.

We also disclose a method of producing a composition for reducing an insect population. The method includes the following steps: submerging a mesh bag containing citrus pulp in a mixture of apple cider vinegar and water, retaining the mesh bag containing citrus pulp in the mixture of apple cider vinegar and water for at least two hours; adding sodium lauryl sulfate; adding ethyl lactate; adding malic acid; removing the mesh bag containing the citrus pulp. Mixing the remaining mixture at 30 RPM. Mixing occurs in the absence of anti-foaming agents (such as but not limited to alcohol).

While various embodiments of the invention have been described, it will be apparent to those of ordinary skill in the art that many more embodiments and implementations are possible that are within the scope of the invention. For instance, steps of a method as displayed in the figures or reflected in the claims do not require a specific order of execution by way they are presented, unless specified. The disclosed steps are listed as exemplary such that additional or different steps may be executed or the steps may be executed in a different order.

The invention claimed is:

1. A method for producing a composition for reducing an insect population, the method comprising the steps of: submerging a mesh bag containing citrus pulp in a mixture of apple cider vinegar and water; retaining the mesh bag containing citrus pulp in the mixture of apple cider vinegar and water for at least two hours; adding sodium lauryl sulfate; adding ethyl lactate; adding malic acid; removing the mesh bag containing the citrus pulp to create a remaining mixture; and mixing the remaining mixture at 30 RPM.

2. The method of claim 1, wherein mixing the remaining mixture takes place in the absence of anti-foaming agents.

3. The method of claim 1, further comprising adding a coloring component; the coloring component selected from the group consisting of red food dye and pink food dye.

* * * * *